United States Patent [19]

Hesse et al.

[11] Patent Number: 4,952,742

[45] Date of Patent: Aug. 28, 1990

[54] PREPARATION OF POLYUNSATURATED HYDROCARBONS

[75] Inventors: Michael Hesse, Ludwigshafen; Rainer Becker, Bad Durkheim, both of Fed. Rep. of Germany

[73] Assignee: BASF Aktiengesellschaft, Ludwigshafen, Fed. Rep. of Germany

[21] Appl. No.: 349,833

[22] Filed: May 10, 1989

[30] Foreign Application Priority Data

May 14, 1988 [DE] Fed. Rep. of Germany ....... 3816576

[51] Int. Cl.$^5$ .......................... C07C 4/04; C07C 2/00; C07C 4/00; C07C 1/00
[52] U.S. Cl. .................... 585/534; 585/600; 585/608; 585/609; 585/640
[58] Field of Search ............... 585/534, 600, 608, 609, 585/640

[56] References Cited

U.S. PATENT DOCUMENTS

| | | | |
|---|---|---|---|
| 2,197,956 | 4/1940 | Vaughn | 585/534 |
| 2,524,866 | 10/1950 | Winslow | 585/534 |
| 2,949,493 | 8/1960 | Happel et al. | 585/534 |
| 2,956,091 | 2/1961 | Manninen et al. | 585/534 |
| 3,283,027 | 11/1966 | Lundeen et al. | 585/534 |
| 3,401,210 | 9/1968 | de Jongh et al. | 585/534 |
| 4,783,546 | 11/1988 | Burke et al. | |

FOREIGN PATENT DOCUMENTS

| | | | |
|---|---|---|---|
| 2052781 | 5/1972 | Fed. Rep. of Germany. | |
| 571470 | 9/1977 | U.S.S.R. | 585/534 |
| 859346 | 8/1981 | U.S.S.R. | 585/640 |
| 1435887 | 5/1976 | United Kingdom. | |

OTHER PUBLICATIONS

Hoelderich, 28 Stud. Surf. Sci. Catal., 827–834 (1986).

*Primary Examiner*—Asok Pal
*Assistant Examiner*—J. Saba
*Attorney, Agent, or Firm*—Keil & Weinkauf

[57] ABSTRACT

Polyunsaturated hydrocarbons of the formula

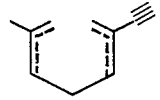

are prepared from unsaturated alcohols of the formula

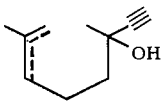

in the presence of zeolite catalysts, in particular zeolites of the pentasil type.

20 Claims, No Drawings

PREPARATION OF POLYUNSATURATED HYDROCARBONS

The present invention relates to a process for preparing polyunsaturated hydrocarbons by water elimination from corresponding alcohols in the presence of catalysts.

It is known that simple acetylene alcohols such as 3-methylpentynol can be dehydrated with $CuSO_4$ (C.r. 243 (1956), 851). In the case of dehydrolinalool, however, the pronounced instability not only of the starting materials but also of the products, for example the polymerization and cyclization tendency owing to the additional double bond in the molecule, largely rules out any similar approach. DE-A No. 2,052,781 describes a specific process which basically likewise relies on the catalytic effect of copper sulfate and is carried out in the liquid phase. It is true that this process makes the desired substance available in principle, but there are appreciable problems with putting it into industrial practice. Yet there is a need in particular for an industrial technique for preparing the secondary products described in DE-A No. 2,502,767. For instance, the previously mentioned instability prevents the transfer into larger reaction units, since this reduces the yield considerably and jeopardizes safe reaction management.

For this reason, there is an urgent need for a new and ideally continuous process which avoids recourse to a liquid reaction phase.

We have found that this object is achieved, and the above-described disadvantages avoided, by preparing polyunsaturated hydrocarbons of the formula I

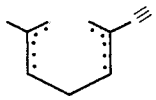

by converting unsaturated alcohols of the formula II

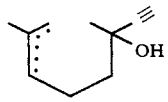

in the presence of zeolites as catalysts.

The process is suitable in particular for the dehydrating conversion of dehydrolinalool in the gas phase over zeolites.

The catalysts used for the process according to the invention are zeolitic catalysts. Zeolites are crystalline aluminosilicates possessing a highly ordered structure having a rigid three-dimensional network of $SiO_4$ or $AlO_4$ tetrahedra joined by common oxygen atoms. The ratio of the Si and Al atoms to oxygen is 1:2. The electrovalence of the aluminum-containing tetrahedra is balanced by the inclusion in the crystal of cations, for example an alkali metal or hydrogen ion. A cation exchange is possible. The spaces between the tetrahedra prior to dehydration by drying and/or calcining are occupied by water molecules.

In zeolites, the aluminum in the lattice can also be replaced by other elements such as B, Ga, Fe, Cr, V, As, Sb or Be, or the silicon can be replaced by a tetravalent element such as Ge, Ti, Zr or Hf.

Zeolites are subdivided by structure into various groups. For instance, in the mordenite group the zeolite structure is formed by chains and in the chabazite group it is formed by layers of tetrahedra, while in the faujasite group the tetrahedra are arranged in polyhedra, for example in the form of a cuboctahedron composed of 4-rings or 6-rings. Depending on how the cuboctahedra are linked together to form voids and pores of different sizes, zeolites are classed as type A, L, X or Y.

Catalysts suitable for the process according to the invention are zeolites of the mordenite group or narrow-pored zeolites of the erionite or chabazite type or zeolites of the faujasite type, for example Y-, X- or L-zeolites.

It is particularly advantageous to use zeolites of the pentasil type. Their common feature is a 5-ring composed of $SiO_4$ tetrahedra. They typically have a high $SiO_2/Al_2O_3$ ratio and pore sizes between those of zeolites of type A and those of type X or Y.

The usable zeolites can have different chemical compositions; suitability is possessed for example by aluminosilicate, borosilicate, iron silicate, beryllium silicate, gallium silicate, chromium silicate, arsenic silicate, antimony silicate and bismuth silicate zeolites and mixtures thereof and by aluminogermanate, borogermanate, gallium germanate and iron germanate zeolites and mixtures thereof. Particular suitability for the process according to the invention is possessed by the aluminosilicate, borosilicate and iron silicate zeolites of the pentasil type. The aluminosilicate zeolite is prepared for example from an aluminum compound, preferably $Al(OH)_3$ or $Al_2(SO_4)_3$, and a silicon component, preferably finely divided silica, in aqueous amine solution, in particular in polyamines such as 1,6-hexanediamine or 1,3-propanediamine or triethylenetetramine solution, in the presence or in particular in the absence of alkali metal or alkaline earth metal at from 100° to 220° C. under autogenous pressure. This also includes the isotactic zeolites described in EP No. 0,034,727. The aluminosilicate zeolites obtained have, depending on the choice of starting material quantitites, an $SiO_2/Al_2O_3$ ratio of from 10 to 40000. It is also possible to synthesize such aluminosilicate zeolites in an ethereal medium such as diethylene glycol dimethyl ether, in an alcoholic medium such as methanol or 1,4-butanediol or in water.

The borosilicate zeolite is synthesized for example at from 90° to 200° C. under autogenous pressure by making a boron compound, for example $H_3BO_3$, react with a silicon compound, preferably finely divided silica, in an aqueous amine solution, in particular 1,6-hexanediamine or 1,3-propanediamine or triethylenetetramine solution, in the presence or in particular in the absence of alkali metal or alkaline earth metal. Even isotactic borosilicate zeolites prepared as described in EP No. 0,034,727 are advantageous to use. It is also possible to use borosilicate zeolites recrystallized not from an aqueous amine solution but from an ethereal solution, for example diethylene glycol dimethyl ether, or from an alcoholic solution, for example 1,6-hexanediol.

The usable high-silicon zeolites ($SiO_2/Al_2O_3$ greater than or equal to 10) also include the known ZSM types and also ferrierite and NU-1 plus Silicalite ®, a silica polymorph molecular sieve.

The aluminosilicate and borosilicate zeolites thus prepared and after they have been isolated, dried at from 100° to 160° C., preferably at 110° C., and calcined at from 450° to 550° C., preferably at 500° C., can be molded with a binder in a ratio of from 90:10 to 40:60% by weight into extrudates or pellets. Suitable binders are various aluminum oxides, preferably boehmite, amorphous aluminosilicates having an $SiO_2/Al_2O_3$ ratio of from 25:75 to 90:5, preferably 75:25, silica, preferably finely divided $SiO_2$, $TiO_2$, mixtures of finely divided $SiO_2$ and finely divided $Al_2O_3$, and clay. After molding, the extrudates or pellets are dried at 110° C. for 16 hours and calcined at 500° C. for 16 hours.

Highly suitable catalysts are also obtained by molding the isolated aluminosilicate or borosilicate zeolite directly after drying and not subjecting it to a calcination until after molding. The aluminosilicate and borosilicate zeolites can be used in the pure form, without binders, as extrudates or pellets, in which case it is possible to use as extrusion or pelletization aids for example ethylcellulose, stearic acid, potato starch, formic acid, oxalic acid, acetic acid, nitric acid, ammonia, amines, silicoesters and graphite or mixtures thereof.

If the zeolite, owing to its manner of preparation, is present not in the catalytically active, acidic H-form but for example in the Na-form, then it can be completely or partially converted into the desired H-form by ion exchange, for example with ammonium ions, and subsequent calcination or by treatment with acids.

If in the course of the use of the zeolitic catalysts according to the invention deactivation occurs due to coking, it is advisable to regenerate the zeolites by burning off the coke deposit with air or with an air/$N_2$ mixture at from 400° to 550° C., preferably 500° C. This restores the zeolites back to their initial activity.

By partial precoking it is possible to adjust the activity of the catalyst to optimum selectivity in respect of the desired reaction product.

To obtain maximum selectivity, high conversion and long lifetimes, it is advantageous to modify the catalysts. A suitable way of modifying the catalysts comprises for example doping the unmolded or molded zeolites with metal salts by ion exchange or by impregnation. The metals used are alkali metals, such as Li, K and Cs, alkaline earth metals, such as Mg, Ca and Ba, earth metals, such as B, Al or Ga, transition metals, such as Cu, Zn, Cr, Mn, Fe, Co, Ni, W and Mo, noble metals, such as Pd, Pt, Rh and Ir, and rare earth metals, such as Ce, La, Pr and Nd.

Advantageously, doping is effected by for example introducing the molded zeolite into a riser pipe and passing for example an aqueous or ammoniacal solution of a halide or nitrate of the above-described metals over it at from 20° to 100° C. Such an ion exchange can be effected for example on the hydrogen, ammonium or alkali metal form of the zeolite. A further way of applying metal to the zeolite comprises impregnating the zeolitic material with for example a halide, a nitrate or an oxide of the above-described metals in aqueous, alcoholic or ammoniacal solution. Both ion exchange and impregnation are followed by at least a drying step, alternatively by a further calcination.

A possible embodiment comprises for example dissolving $Cu(NO_3)_2 \times 3\ H_2O$ or $Co(NO_3)_2 \times 6\ H_2O$ or $Ce(NO_3)_3 \times 6\ H_2O$ or $La(NO_3)_3 \times 6\ H_2O$ or $Cs_2CO_3$ in water. The solution is used to impregnate the molded or unmolded zeolite for a certain time, about 30 minutes. Any supernatant solution is stripped of water in a rotary evaporator. The impregnated zeolite is then dried at about 150° C. and calcined at 550° C. This impregnating step can be carried out a number of times in succession in order to obtain the desired metal content.

It is also possible for example to prepare an aqueous $Co(NO_3)_2$ solution and to suspend the pure pulverulent zeolite therein at from 40° to 100° C. by stirring for about 24 hours. After filtration, drying at about 150° C., and calcination at about 500° C., the zeolitic material thus isolated can be further processed, with or without a binder, into extrudates, pellets or fluidizable material.

An ion exchange with the zeolite present in the H-form or ammonium form or alkali form can be effected by introducing the zeolite in extrudate or pellet form into a column and passing for example an aqueous $Co(NO_3)_2$ solution over it at a slightly elevated temperature of from 30° to 80° C. for from 15 to 20 hours with recirculation. This is followed by washing with water, drying at about 150° C. and calcining at about 550° C.

With some metal-doped zeolites, for example Pd-, Cu- or Ni-doped zeolites, an aftertreatment with hydrogen is advantageous.

A further method of modification comprises subjecting the molded or unmolded zeolitic material to a treatment with acids such as hydrochloric acid, hydrofluoric acid and phosphoric acid and/or water vapor. This is advantageously done for example by treating zeolites in powder form with 1N phosphoric acid at 80° C. for 1 hour. The treatment is followed by washing with water, drying at 110° C. for 16 hours and calcining at 550° C. for 20 hours. Alternatively, zeolites, before or after they have been molded with binders, are for example treated with from 3 to 25% strength by weight, in particular from 12 to 20% strength by weight, aqueous hydrochloric acid at from 60° to 80° C. for from 1 to 3 hours. The zeolite thus treated is then washed with water, dried and calcined at from 400° to 500° C.

A particular embodiment of the acid treatment comprises treating the unmolded zeolitic material at elevated temperature with hydrofluoric acid, in general with from 0.001N to 2N, preferably from 0.05N to 0.5N, hydrofluoric acid, for example by refluxing for in general from 0.5 to 5 hours, preferably from 1 to 3 hours. After isolation, for example by filtration and washing, the zeolitic material is advantageously dried, for example at from 100° C. to 160° C., and calcined, in general at from 450° to 600° C. In a further preferred embodiment of the acid treatment, the zeolitic material, after it has been molded with a binder, is treated at elevated temperature, advantageously at from 50° to 90° C., with hydrochloric acid, in general with from 3 to 25% strength by weight hydrochloric acid, preferably with from 12 to 20% strength by weight hydrochloric acid, for preferably from 1 to 3 hours. The zeolitic material is then in general washed and advantageously dried, for example at from 100° to 160° C., and calcined, in general at from 450° to 600° C. Even a successive treatment with HF and HCl may in certain circumstances be advantageous.

The catalysts described herein can be used as a matter of choice in the form of from 2 to 4 mm extrudates, as pellets from 3 to 5 mm in diameter, as chips from 0.1 to 0.5 mm in particle size, or as fluidizable material.

The reaction conditions chosen in general for the conversion according to the invention are in the preferred gas phase reaction from 100° to 500° C., preferably from 200° to 350° C., at a weight hourly space velocity (WHSV) of from 0.1 to 20 $h^{-1}$, preferably from 0.5 to 5 $h^{-1}$ (g of starting mixture per g of catalyst per hour). The reaction can be carried out in a fixed bed or in a fluidized bed.

However, it is also possible to carry out the reaction in the liquid phase (by the suspension, trickle bed or liquid phase procedure) at from 50° to 300° C., preferably at from 100° to 250° C., at a g of starting material: g of catalyst ratio of from 100:1 to 5:1, preferably from 60:1 to 10:1.

The process is in general carried out under atmospheric pressure or, depending on the volatility of the starting compound, under reduced pressure or superatmospheric pressure. The process is preferably carried out continuously.

After the reaction the resulting products are isolated from the reaction mixture in a conventional manner, for example by distillation; unconverted starting materials are if appropriate recycled.

The Examples illustrate the invention.

EXAMPLES 1 TO 11

The reaction is carried out in the gas phase under isothermal conditions in a tubular reactor (coil, 0.6 cm inner diameter, 90 cm length) for not less than 6 hours. The reaction products are separated off in a conventional manner and characterized by GC/MS, NMR and melting point determination. The quantitative determination of the reaction products and the starting materials is done by gas chromatography. The starting material used is in all cases dehydrolinalool (2,6-dimethyl-2-octen-7-yn-6-ol).

EXAMPLES 12 TO 15

Procedure as in Examples 1 to 11, but with the addition of equal amounts of water to the reaction solution.

The catalysts used for the process according to the invention are:

Catalyst A

The borosilicate zeolite of the pentasil type is prepared in a hydrothermal synthesis from 640 g of finely divided $SiO_2$, 122 g of $H_3BO_3$ and 8000 g of an aqueous 1,6-hexanediamine solution (mixture 50:50% by weight) at 170° C. under autogenous pressure in a stirred autoclave. Following filtration and washing the crystaline reaction product is dried at 100° C. for 24 hours and calcined at 500° C. for 24 hours. This borosilicate zeolite is composed of 94.2% by weight of $SiO_2$ and 2.3% by weight of $B_2O_3$.

This material is molded with a molding aid into 2-mm extrudates which are dried at 110° C. for 16 hours and calcined at 500° C. for 24 hours.

Catalyst B

An aluminosilicate zeolite of the pentasil type is prepared under hydrothermal conditions at autogenous pressure and 150° C. from 650 g of finely divided $SiO_2$ and 203 g of $Al_2(SO_4)_3 \times 18\ H_2O$ in 10 kg of an aqueous 1,6-hexanediamine solution (mixture 50:50% by weight) in a stirred autoclave. Following filtration and washing the crystalline reaction product is dried at 100° C. for 24 hours and calcined at 500° C. for 24 hours. This aluminosilicate zeolite contains 92.8% by weight of $SiO_2$ and 4.2% by weight of $Al_2O_3$. This material is molded with a molding aid into 2-mm extrudates which are dried at 110° C. for 16 hours and calcined at 500° C. for 24 hours.

The extrudates thus obtained are impreganted with aqueous copper nitrate solution, then dried at 130° C. for 2 hours and calcined at 540° C. for 2 hours. The Cu content is 3.5% by weight.

Catalyst C

Catalyst C is prepared by molding a commercial Na-Y zeolite in powder form with boehmite (weight ratio 60:40) into 2 mm extrudates which are dried at 110° C. for 16 hours and calcined at 500° C. for 16 hours.

The extrudates are ion exchanged with 20% strength $NH_4Cl$ solution (weight ratio 1:15) at 80° C. This is followed by washing free of chloride, drying at 110° C. and calcining at 500° C. for 5 hours. The Na content is 0.07%.

Catalyst D

An aluminosilicate zeolite of the ZSM-5 type is prepared under hydrothermal conditions at autogenous pressure and 170° C. from 13.2 g of silica sol (30% by weight of $SiO_2$), 314 g of sodium hydroxide, 3.36 kg of aqueous tetra-n-propylammonium hydroxide solution (20% strength) and 6.4 kg of water in a stirred autoclave. Following filtration and washing, the crystalline reaction product is dried at 110° C. for 24 hours and calcined at 500° C. for 24 hours. This zeolite is characterized by the following composition: 81.4% by weight of $SiO_2$, 0.20% by weight of $Al_2O_3$ and 1.0% by weight of Na.

This zeolite is molded with a molding aid into 2-mm extrudates. These are dried at 110° C. for 16 hours and calcined at 110° C. for 16 hours and calcined at 500° C. for 16 hours.

The extrudates are ion exchanged four times with 20% strength by weight $NH_4Cl$ solution (15 ml of solution/g of extrudate) at 80° C. in a riser pipe. The extrudates are then washed free of chloride, dried at 110° C. for 10 hours and thereafter calcined at 500° C. for 5 hours. The Na content is then 0.02% by weight.

Catalyst E

Catalyst E is obtained by impregnating the extrudates of catalyst C with aqueous cerium nitrate solution, then drying at 130° C. for 2 hours and calcining at 540° C. for 2 hours. The Ce content is 2.9% by weight.

Catalyst F

The borosilicate zeolite of the pentasil type is prepared in a hydrothermal synthesis from 740 g of finely divided $SiO_2$, 360 g of $H_3BO_3$ and 9.7 kg of aqueous 1,6-diaminohexane solution (50% by weight of amine) at 165° C. under autogenous pressure in a stirred autoclave. Following filtration and washing, the crystalline reaction product is dried at 160° C. for 24 hours and calcined at 500° C. for 24 hours. This borosilicate zeolite is composed of 92.9% by weight of $SiO_2$ and 2.92% by weight of $B_2O_3$.

The borosilicate zeolite is refluxed with 0.08N HF (3.6 g of HF solution/g of zeolite) for 1 hour. The zeolite is then filtered off, washed, dried at 110° C. and calcined at 500° C. for 5 hours.

The treated borosilicate zeolite is molded with an amorphous aluminosilicate (weight ratio $SiO_2$:$Al_2O_3$ = 75:25) in a weight ratio of 60:40 in the presence of a molding aid into 2-mm extrudates, which are dried at 110° C. for 16 hours and calcined at 500° C. for 16 hours.

The F content of the catalyst is 0.055% by weight.

Catalyst G

Catalyst G is obtained by molding the borosilicate zeolite (cf. catalyst A) with boehmite (weight ratio 60:40) into 2-mm extrudates, which are dried at 110° C. for 16 hours and calcined at 500° C. for 16 hours.

Catalyst H

Catalyst H is obtained by impregnating the extrudates of catalyst A with aqueous copper nitrate solution, then drying at 130° C. for 2 hours and calcining at 540° C. for 2 hours. The Cu content is 1.6% by weight.

Catalyst I

Catalyst I is obtained by impregnating the extrudates of catalyst G with aqueous copper nitrate solution, then drying at 130° C. for 2 hours and calcining at 540° C. for 2 hours. The Cu content is 3.5% by weight.

| Example | Catalyst | Temperature [°C.] | Conversion [%] | Content of Compound I (mixture of isomers) Reacted Organic Phase [%] |
| --- | --- | --- | --- | --- |
| 1 | A | 250 | 50 | 58 |
| 2 | A | 300 | 44 | 77 |
| 3 | C | 300 | 77 | 64 |
| 4 | E | 300 | 74 | 72 |
| 5 | D | 300 | 10 | 0 |
| 6 | F | 250 | 89 | 58 |
| 7 | F | 300 | 81 | 68 |
| 8 | H | 250 | 64 | 64 |
| 9 | H | 300 | 100 | 10 |
| 10 | B | 250 | 63 | 61 |
| 11 | B | 300 | 100 | 1 |
| 12 | F | 300 | 93 | 85 |
| 13 | G | 300 | 70 | 79 |
| 14 | G | 350 | 72 | 73 |
| 15 | I | 300 | 100 | 54* |

Values after 2-hour runs
*: after a 4-hour run

The reacted organic phase contains a mixture of the isomers 2,6-dimethyl-2,5-octadien-7-yne (dehydroocimene) and 2-methyl-6-methylene-2-octen-7-yne (dehydromyrcene).

We claim:

1. A process for preparing a polyunsaturated hydrocarbon of the formula I

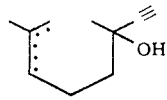

which comprises converting an unsaturated alcohol of the formula II

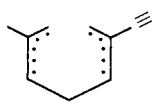

in the presence of a zeolite catalyst.

2. The process of claim 1, wherein an isomeric mixture of 2,6-dimethyl-2,5-octadien-7-yne (dehydroocimene) and 2-methyl-6-methylene-2-octen-7-yne (dehydromyrcene) is prepared by water elimination from 2,6-dimethyl-2-octen-7-yn-6-ol (dehydrolinalool) in the presence of a zeolite catalyst.

3. The process of claim 1, wherein the catalyst used is a penlasil zeolite.

4. The process of claim 1, wherein the catalyst used is an aluminosilicate zeolite.

5. The process of claim 1, wherein the catalyst used is a borosilicate zeolite.

6. The process of claim 1, wherein the catalyst used is an iron silicate zeolite.

7. The process of claim 1, wherein the catalyst used is faujasite zeolite.

8. The process of claim 1, wherein the catalyst used is a zeolite doped with a transition metal.

9. The process of claim 1, wherein the catalyst used is a zeolite doped with a rare earth metal.

10. The process of claim 9, wherein the catalyst used is a zeolite doped with Ce or La.

11. The process of claim 1, wherein the catalyst used is an acid-treated zeolite.

12. The process of claim 13, wherein the catalyst is an aluminosilicate, borosilicate or iron silicate pentasil zeolite.

13. The process of claim 1, wherein the unsaturated alcohol (II) is converted in the gas phase at a temperature of from 100° to 500° C.

14. The process of claim 13, wherein the conversion is carried out at from 200° to 350° C.

15. The process of claim 1, wherein the unsaturated alcohol (II) is converted in the gas phase at from 200° to 350° C. at a weight hourly space velocity of from 0.1 to 20 $h^{-1}$.

16. The process of claim 15, wherein the conversion is carried out at a weight hourly space velocity of from 0.5 to 5 $h^{-1}$.

17. The process of claim 1, wherein the unsaturated alcohol (I) is converted in the liquid phase at a temperature of from 50° to 300° C. and the ratio of alcohol (II) to catalyst is from 100:1 to 5:1.

18. The process of claim 17, wherein the temperature is from 100° to 250° C. and the ratio of alcohol (II) to catalyst is from 60:1 to 10:1.

19. The process of claim 1, wherein the unsaturated alcohol II is 2,6-dimethyl-2-octen-7-yn-6-ol and the conversion occurs in the gas phase at 200° to 350° C. at a weight hourly space velocity of from 0.5 to 5 $h^{-1}$.

20. The process of claim 1, wherein the catalyst is an aluminosilicate, borosilicate, or iron silicate pentasil zeolite, the unsaturated alcohol (II) is 2,6-dimethyl-2-octen-7-yn-6-ol, and the conversion occurs in the gas phase at a temperature of from 200° to 350° C. at a weight hourly space velocity of from 0.5 to 5 $h^{-1}$.

* * * * *

UNITED STATES PATENT AND TRADEMARK OFFICE
CERTIFICATE OF CORRECTION

PATENT NO. : 4,952,742

DATED : August 28, 1990

INVENTOR(S) : Michael HESSE et al.

It is certified that error appears in the above-identified patent and that said Letters Patent is hereby corrected as shown below:

IN THE CLAIMS   Column 8, line 15,

Claim 3: "penlasil" should read --pentasil--

Signed and Sealed this

Twelfth Day of November, 1991

Attest:

HARRY F. MANBECK, JR.

*Attesting Officer*    *Commissioner of Patents and Trademarks*